(12) United States Patent
Greenberg et al.

(10) Patent No.: US 10,092,391 B2
(45) Date of Patent: Oct. 9, 2018

(54) ENDOLUMINAL PROSTHESIS HAVING MODULAR BRANCHES AND METHODS OF DEPLOYMENT

(71) Applicants: COOK MEDICAL TECHNOLOGIES LLC, Bloomington, IN (US); CLEVELAND CLINIC FOUNDATION, Cleveland, OH (US); Alicia Fanning, Bratenahl, OH (US)

(72) Inventors: Roy K. Greenberg, Bratenahl, OH (US); Blayne A. Roeder, Bloomington, IN (US)

(73) Assignees: The Cleveland Clinic Foundation, Cleveland, OH (US); Cook Medical Technologies LLC, Bloomington, IN (US)

( * ) Notice: Subject to any disclaimer, the term of this patent is extended or adjusted under 35 U.S.C. 154(b) by 124 days.

(21) Appl. No.: 14/139,381

(22) Filed: Dec. 23, 2013

(65) Prior Publication Data
US 2014/0180394 A1   Jun. 26, 2014

Related U.S. Application Data

(60) Provisional application No. 61/746,029, filed on Dec. 26, 2012.

(51) Int. Cl.
*A61F 2/06* (2013.01)
*A61F 2/07* (2013.01)

(52) U.S. Cl.
CPC .......... *A61F 2/07* (2013.01); *A61F 2002/061* (2013.01); *A61F 2002/067* (2013.01)

(58) Field of Classification Search
CPC .......... A61F 2002/061; A61F 2002/067; A61F 2002/065; A61F 2002/821; A61F 2002/826; A61F 2002/072; A61F 2002/075; A61F 2002/077; A61F 2/82
USPC ...................... 623/1.13–1.16, 1.35
See application file for complete search history.

(56) References Cited

U.S. PATENT DOCUMENTS

| 5,425,765 A | 6/1995 | Tiefenbrun et al. |
| 5,824,040 A | 10/1998 | Cox et al. |
| 6,162,246 A * | 12/2000 | Barone ............ A61F 2/07 623/1.1 |
| 6,344,056 B1 * | 2/2002 | Dehdashtian ........ 623/1.35 |
| 6,395,018 B1 | 5/2002 | Castaneda |

(Continued)

FOREIGN PATENT DOCUMENTS

| JP | 2002506661 A | 3/2002 |
| JP | 2008541949 A | 11/2008 |

(Continued)

*Primary Examiner* — Diane Yabut
*Assistant Examiner* — Erich Herbermann
(74) *Attorney, Agent, or Firm* — Brinks Gilson & Lione

(57) ABSTRACT

The present embodiments provide an endoluminal prosthesis having modular branches, and systems and methods for facilitating deployment of the endoluminal prosthesis. In one example, the endoluminal prosthesis comprises a graft including a bifurcated body of a biocompatible material. The bifurcated body includes distally extending limbs. Limb extensions can be longitudinally and circumferentially adjusted prior to mating with the limbs to enable an "off-the-shelf" prosthesis that can conform to various complex anatomy. When adjusted and mated, fenestrations in the limb extensions can align with branch vessels.

24 Claims, 14 Drawing Sheets

(56) References Cited

U.S. PATENT DOCUMENTS

| | | | |
|---|---|---|---|
| 7,144,421 B2* | 12/2006 | Carpenter | A61F 2/07 623/1.31 |
| 7,407,509 B2 | 8/2008 | Greenberg et al. | |
| 7,828,837 B2 | 11/2010 | Khoury | |
| 7,846,194 B2 | 12/2010 | Hartley et al. | |
| 2002/0058986 A1* | 5/2002 | Landau et al. | 623/1.13 |
| 2004/0117003 A1 | 6/2004 | Ouriel et al. | |
| 2005/0033406 A1 | 2/2005 | Barnhart et al. | |
| 2006/0161244 A1 | 7/2006 | Seguin | |
| 2006/0229707 A1* | 10/2006 | Khoury | A61F 2/07 623/1.16 |
| 2006/0247761 A1 | 11/2006 | Greenberg et al. | |
| 2007/0173929 A1* | 7/2007 | Boucher et al. | 623/1.35 |
| 2008/0262595 A1 | 10/2008 | Chu et al. | |
| 2009/0043377 A1 | 2/2009 | Greenberg et al. | |
| 2010/0249899 A1 | 9/2010 | Chuter et al. | |
| 2010/0305686 A1 | 12/2010 | Cragg et al. | |
| 2011/0130825 A1 | 6/2011 | Cragg et al. | |
| 2011/0196477 A1 | 8/2011 | Ganesan et al. | |
| 2012/0290068 A1 | 11/2012 | Roeder et al. | |
| 2013/0211505 A1* | 8/2013 | Robison | 623/1.35 |
| 2013/0289713 A1* | 10/2013 | Pearson et al. | 623/1.35 |

FOREIGN PATENT DOCUMENTS

| | | | |
|---|---|---|---|
| WO | WO 1997-017910 A1 | 5/1997 | |
| WO | 98/53761 A1 | 12/1998 | |
| WO | 9913808 A1 | 3/1999 | |
| WO | 2006130755 A2 | 12/2006 | |
| WO | 2007/124053 A1 | 11/2007 | |
| WO | 2009/102439 A1 | 8/2009 | |
| WO | 20101127040 A1 | 11/2010 | |

* cited by examiner

ENDOLUMINAL PROSTHESIS HAVING MODULAR BRANCHES AND METHODS OF DEPLOYMENT

CROSS-REFERENCE TO RELATED APPLICATIONS

This application claims the benefit of U.S. Provisional Patent Application No. 61/746,029, filed Dec. 26, 2012, which is hereby incorporated by reference in its entirety herein.

BACKGROUND

The present embodiments relate generally to an endoluminal prosthesis having modular branches, and systems and methods for facilitating deployment of such an endoluminal prosthesis.

Using stent grafts to treat aneurysms is common in the medical field. Stent grafts may be deployed by accessing a vasculature with a small incision in the skin and guiding a delivery system to the target area. This intraluminal delivery is less invasive and generally preferred over more intrusive forms of surgery. Multiple stent grafts may be implanted using intraluminal delivery to provide a system of interconnected stent grafts. Interconnected stent grafts can be made of fenestrated stent grafts and smaller side branch stent grafts, including bifurcated components.

Sometimes aneurysms engulf a vessel and its branch vessels, such as the aorta and the renal arteries, the aortic arch and the branch arteries, or the iliac arteries. In such instances, a fenestrated graft can be implanted in the main vessel while smaller branch grafts can be deployed in the branch arteries. The main vessel grafts have fenestrations that correspond with the openings of the branch vessels. The smaller branch grafts are joined with the main vessel graft at the fenestrations. Due to the torsion and rigors of the endovascular system, this juncture can be subject to significant stress.

Moreover, when a condition such as an aneurysm has engulfed a main vessel and multiple branch vessels, it may be relatively time consuming to deliver the smaller branch grafts needed in addition to the main graft. For example, insertion of wire guides and delivery devices may be time consuming and/or difficult to perform when multiple smaller branch grafts are deployed to cannulate multiple corresponding branch vessels.

Furthermore, the complex anatomy can vary from patient to patient, such that pre-fabricated grafts having fenestrations therein to correspond to various branch arteries may not be suitable for all patients. Manufacture of grafts that can correspond to a particular patient's anatomy can be undesirably time consuming.

Juxtarenal aneurysms, thoracoabdominal aneurysms, and failed endografts or previous open surgical repairs can require deployment of an endoluminal prosthesis such as a graft to repair the failure or aneurysm. Previously placed endografts include a flow divider for diverting flow from the aorta to renal arteries. This results in a short distance between the flow divider and the renal arteries. Given the complex anatomy from patient to patient, repair of a failed graft can be time consuming due to the need to replace the failed graft with a graft having a configuration that can conform to the particular anatomy. Thus, surgeons may have to wait for the prosthesis to be configured to conform to the anatomy, causing an increased time in repairing the failed graft or aneurysm.

SUMMARY

The present embodiments provide an endoluminal prosthesis having modular branches, and systems and methods for facilitating deployment of the endoluminal prosthesis.

In one example, a modular stent-graft apparatus includes a graft comprising biocompatible material, the graft having a proximal and distal end; a generally tubular proximal portion of the graft with a lumen extending therethrough; first and second limb portions of the graft extending distally from a bifurcation point of the proximal portion and having distal ends, the first and second limb portions each having lumens extending therethrough, the lumens of the limb portions being in fluid communication with the proximal portion lumen; at least one limb extension comprising biocompatible material, the at least one limb extension having a proximal end and a distal end and a lumen extending therebetween, the at least one limb extension dimensioned to engage one of the first and second limb portion; and at least one passageway though a sidewall of the at least one limb extension disposed between the proximal and distal ends of the at least one limb extension.

In another form, the system can include a first branch extending from the graft proximal portion and a second branch extending from the graft proximal portion, wherein the first and second branches each have proximal and distal ends and a lumen extending therebetween that is in fluid communication with the graft proximal portion lumen.

In yet another form, the distal ends of the first and second limbs extend approximately the same longitudinal length from the bifurcation point.

In another form, the at least one limb extension comprises a first and second limb extension each having a passageway therein, and the first and second limb extensions are each mated to the first and second limb portions.

In still another form, the passageways in the first and second limb extensions are each located at approximately the same longitudinal distance from the proximal ends thereof, and the passageways are located at different longitudinal distances from the bifurcation point when the first and second limb extensions are mated to the limb portions.

In another form, the distal end of the first limb extends longitudinally farther from the bifurcation point than the distal end of the second limb and the proximal end of the at least one limb extension is mated to the distal end of the second limb.

In another form, the system includes a limb passageway through a sidewall in the first limb disposed between the proximal and distal ends thereof.

In another form, the passageway comprises a fenestration in the at least one limb extension.

In another form, the passageway comprises a branch extending from the at least one limb extension.

In one form, an endoluminal prosthesis includes a graft having a bifurcated body comprising a biocompatible material, the graft having proximal and distal ends and a lumen extending therebetween, the bifurcated body having first and second limb portions extending distally from a generally tubular proximal portion; first and second proximal graft passageways extending through a sidewall of the proximal portion of the graft, and a first limb extension attached to and extending distally from the first limb portion, the first limb extension having a passageway through a sidewall thereof.

In another form, the first limb extension includes a proximal portion and a distal portion, the proximal portion having a smaller diameter than the distal portion when the first limb extension is in the radially expanded condition.

In another form, the first limb extension includes a proximal portion, a distal portion, and an intermediate portion therebetween, the proximal and distal portions having diameters that are smaller than the intermediate portion when the first limb extension is in the radially expanded condition.

In yet another form, the intermediate portion of the first limb extension is greater than the diameter of the first limb portion.

In another form, the second limb portion includes a second passageway through a sidewall thereof.

In one form, a method of delivering an endoluminal prosthesis to a patient's body includes the steps of delivering a bifurcated body having a proximal portion and a distal portion to a vessel of a patient's body, wherein the distal portion includes first and second limb portions extending distally from the proximal portion; delivering, to a distal end of the first limb portion, a first limb extension having a first passageway therein; adjusting the longitudinal and circumferential location of the first passageway to correspond to the location of a first artery ostium; in response to adjusting the location of the first passageway, mating a proximal end of the first limb extension with the distal end of the first limb portion.

In another form, the first and second limb portions are disposed above a patient's renal arteries.

In another form, the method further includes the steps of delivering a second limb extension having a second passageway therein to the second limb portion; adjusting the longitudinal and circumferential location of the second passageway to correspond to the location of a second artery ostium; and in response to adjusting the location of the second passageway, mating a proximal end of the second limb extension with the distal end of the limb portion.

In another form, the method further includes the steps of delivering a first branch extension to the first passageway and mating a proximal end of the first branch extension to the first passageway.

In another form, the method further includes the steps of delivering a first branch extension to the first passageway; mating a proximal end of the first branch extension to the first passageway; delivering a second branch extension to the second passageway; and mating the second branch extension to the second passageway.

In yet another form, the method further includes the steps of delivering and mating a first branch extension to a first branch portion extending from the proximal portion of the bifurcated body and delivering and mating a second branch extension to a second branch portion extending from the proximal portion of the bifurcated body.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 16 FIGS. 16a-g illustrate various types of fenestrations and intermediate branch extensions for use with the endoluminal prosthesis.

DETAILED DESCRIPTION OF THE PREFERRED EMBODIMENTS

In the present application, the term "proximal" refers to a direction that is generally closest to the heart during a medical procedure, while the term "distal" refers to a direction that is furthest from the heart during a medical procedure. When referring to components or portions that mount to or extend from another major component, the term "proximal" refers to the region of the component or portion that is generally closest to the major component during a medical procedure, while the term "distal" refers to the region of the component or portion that is generally furthest from the major component during a medical procedure.

Figure 1A:
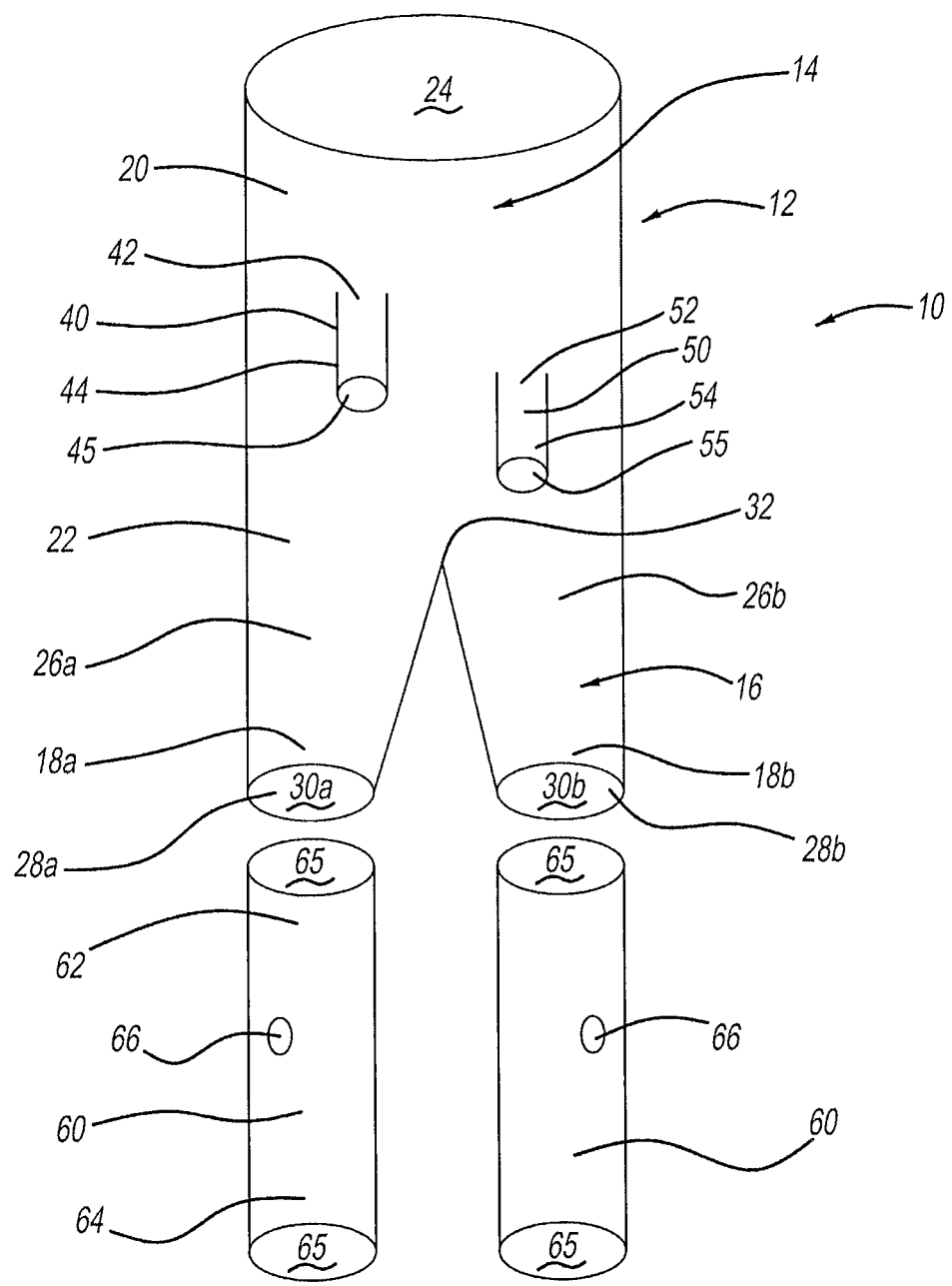
FIG. 1A is an exploded perspective view of a first embodiment of an endoluminal prosthesis having a graft and limb extensions for mating thereto.

Referring now to FIG. 1A, a first embodiment of an endoluminal prosthesis 10 comprises a graft 12 made of a biocompatible material. The graft 12 has a proximal portion 14 and a distal portion 16. The distal portion 16 is bifurcated and includes first and second limbs 18a and 18b extending distally from the proximal portion 14.

The proximal portion 14 can be generally tubular and includes a proximal end 20 and a distal end 22 with a lumen 24 extending therebetween. The limbs 18a and 18b respectively include proximal regions 26a and 26b and distal ends 28a and 28b with lumens 30a and 30b extending therebetween. The limbs 18a and 18b converge with the proximal portion 14 at a bifurcation point 32 so that the lumens 24, 30a, and 30b are in fluid communication, and flow through the proximal portion 14 can thereby be diverted into both of the limbs 18a and 18b.

Many different types of graft materials may be used for the graft 12. Common examples of graft materials currently used include expandable polytetrafluoroethylene (ePTFE), polytetrafluoroethylene (PTFE), Dacron, polyester, fabrics and collagen. However, graft materials may be made from numerous other materials as well, including both synthetic polymers and natural tissues.

In the embodiment of FIG. 1A, the graft 12 includes a first branch 40 having proximal and distal ends 42 and 44 and a lumen 45 extending therebetween. The first branch 40 extends radially outward from the graft 12. The proximal end 42 of the first branch 40 is disposed at a location proximal to the bifurcation point 32.

The graft 12 further comprises a second branch 50 having proximal and distal ends 52 and 54 and a lumen 55 extending therebetween. The second branch 50 extends radially outward from the graft 12. The proximal end 52 of the second branch 50 is disposed at a location proximal to the bifurcation point 32 and distal to the proximal end 42 of the first branch 40, as best seen in FIG. 1A.

The first and second branches 40 and 50 can also extend helically around the graft 12. In another form, the first and second branches 40 and 50 can be in the form of pivot branches extending from a pivot fenestration. In yet another form, the first and second branches 40 and 50 can extend through fenestrations formed in the graft 12, or the graft 12 could simply include fenestrations in place of the first and second branches 40 and 50 to allow for subsequent installation of branch extensions therethrough. As such, the first and second branches 40 and 50, or the alternative fenestrations, can be referred to generally as proximal graft passageways.

When deployed within the patient's body, the first branch 40 is generally adjacent the celiac artery, while the second branch 50 is generally close to the SMA. However, it will be appreciated that other configurations of the first and second branches 40 and 50 could also be used, such as where the second branch 50 is more proximal than the first branch 40, or where the branches 40 and 50 are disposed at approximately the same longitudinal location on the graft 12.

Figure 1C:
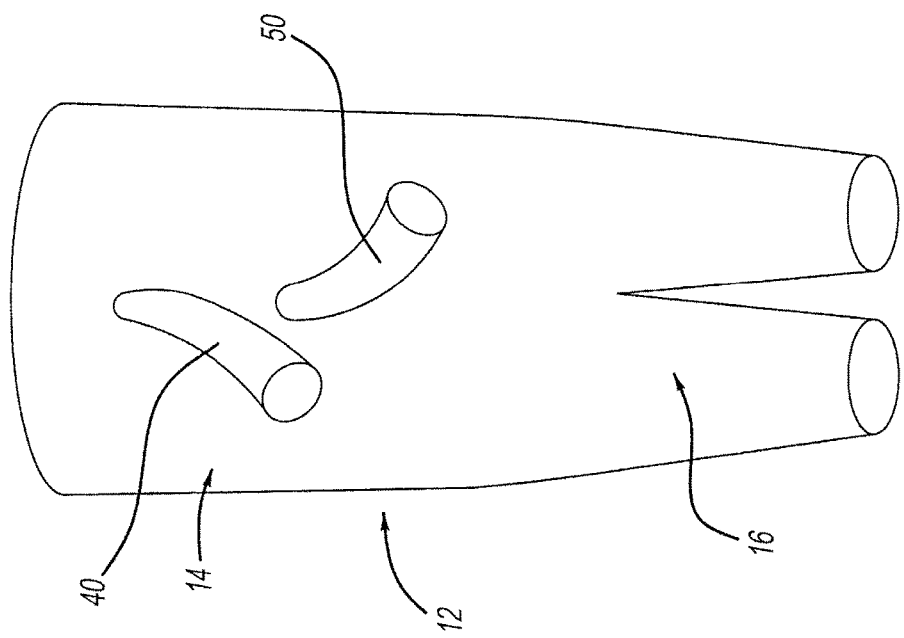
FIG. 1C is a perspective view of the graft having first and second branches extending in a helical manner from the proximal portion of the graft.
Figure 1B:
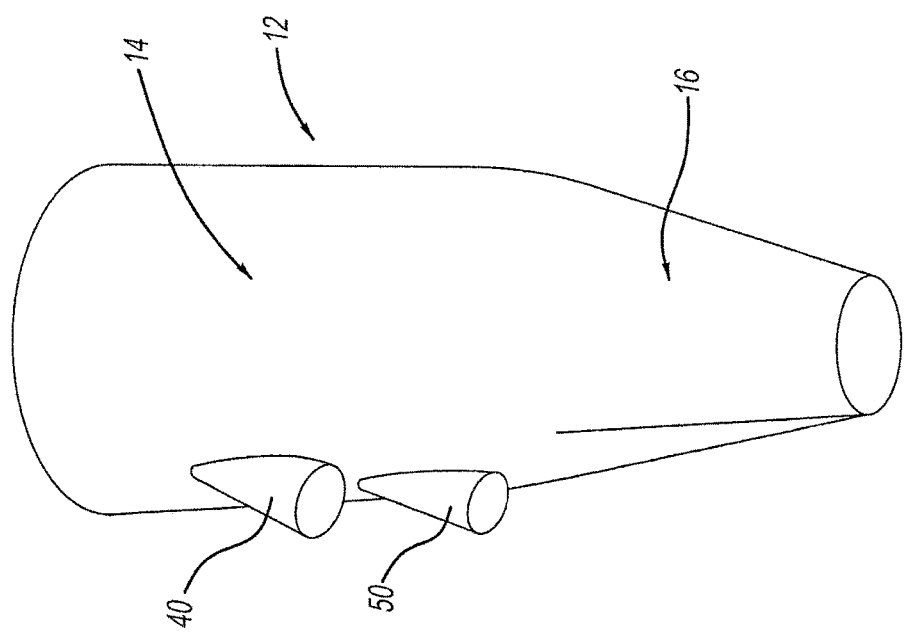
FIG. 1B is perspective view of the graft having first and second branches extending at an angle from a proximal portion of the graft.

In one embodiment, the distal end 44 of the first branch 40 and the distal end 54 of the second branch 50 each extend in a distal direction from their respective proximal ends 42 and 52 toward the distal portion 16 of the graft 12, as shown in FIG. 1A. In one form, as shown in FIG. 1B, the first branch 40 and second branch 50 can be in the form of angled branches, where the branches 40 and 50 extend from the proximal portion 14 distally at an acute angle from the proximal portion 14. In another form, shown in FIG. 1C, the first branch 40 and second branch 50 can be in the form of helical branches, where the branches 40 and 50 extend distally in a helical direction around the proximal portion. Such orientations of the distal regions of the branches 40 and 50 may facilitate insertion of corresponding branch extension prostheses, further described below, when these branch extension prostheses are delivered in a distal direction. For example, in the exemplary method of FIGS. 7-14 shown and described below, branch extension prostheses 240 and 250 are delivered in a proximal to distal direction for the branches 40 and 50 respectively.

However, it will be appreciated that the distal regions 44 and 54 of the branches 40 and 50 could extend in a proximal direction toward the proximal end of the graft proximal region 14, which orientation of the distal regions 44 and 54 may facilitate insertion of corresponding branch extensions that can be delivered in a distal to proximal direction.

In the embodiment of FIG. 1A, the endoluminal prosthesis 10 also includes limb extensions 60. Limb extensions 60 include proximal and distal ends 62 and 64 with a lumen 65 extending therebetween. Each limb extension 60 further includes a fenestration 66 therein that is disposed between the proximal and distal ends 62 and 64. The fenestration 66 may facilitate insertion of a corresponding branch extension prosthesis and is configured to align with a corresponding branch artery, such as the left or right renal arteries.

The fenestrations 66 can have various types and shapes. For example, they may be in the form of a pivot fenestration extending radially outward or a pivot fenestration extending radially inward, as described in U.S. patent application Ser. No. 13/213,349, filed Aug. 19, 2011 and assigned to the assignee of this application, which is hereby incorporated by reference in its entirety. They could also be in the form of diamond fenestrations. The various fenestration types can have a generally circular or circumferentially symmetrical shape, or they could have an oblong shape.

The fenestrations 66 can be disposed approximately 20-35 mm from the proximal ends 62 of the limb extensions 60. However, other locations could also be used to facilitate the use of the limb extensions 60 with differing anatomy.

Figure 3:
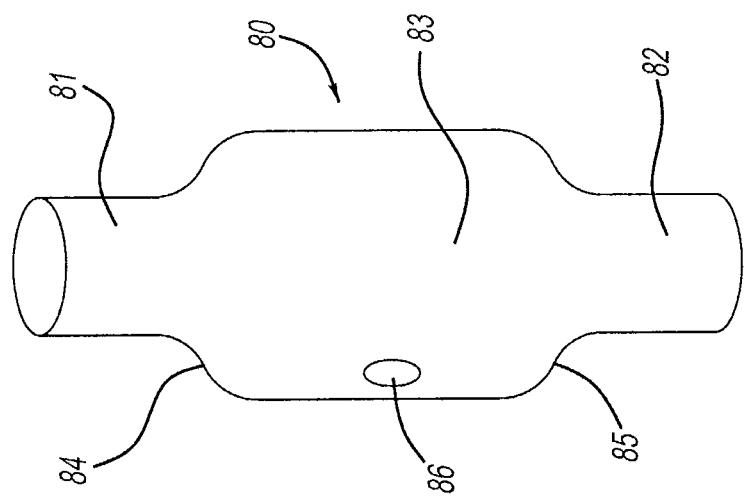
FIG. 3 is a perspective view of an alternative embodiment of a limb extension.
Figure 2:
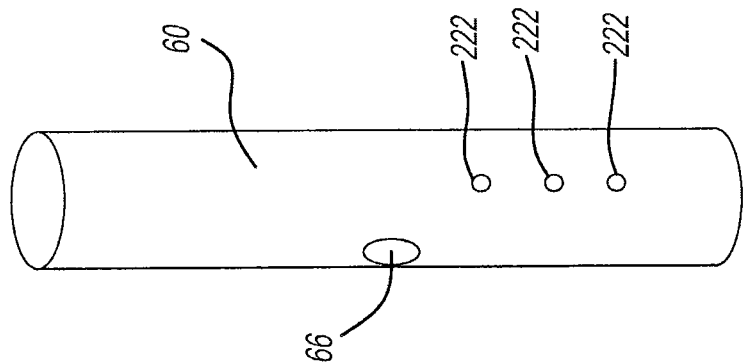
FIG. 2 is a perspective view of the limb extension of FIG. 1A.

As shown in FIG. 2, the limb extensions 60 have a generally constant outer diameter such that they are generally tubular in shape. However, other limb extension shapes can also be used, such as those illustrated in FIGS. 3 and 4. As shown in FIG. 3, a limb extension 80 includes a proximal region 81, a distal region 82, and an intermediate region 83. The intermediate region has a diameter that is greater than both the proximal and distal regions 81 and 82. A first tapered portion 84 extends between the proximal region 81 and the intermediate region 83, with the diameter of the first tapered portion 84 increasing in the distal direction. Similarly, a second tapered portion 85 extends between the distal region and the intermediate region, with the diameter of the second tapered portion 85 increasing in the proximal direction. This configuration can help accommodate a fenestration 86 that is relatively larger than fenestration 66 due to the increased surface area of the limb extension 80 in the intermediate region 83.

In one form, the proximal ends 62 and 81 can have a diameter of approximately 12-13 mm. Accordingly, the distal ends 18a and 18b of the graft 12 can each have a diameter of approximately 12 mm so that the corresponding limb extension can be securely mated thereto. In the case of the limb extension 80, the intermediate region 83 can have a diameter of approximately 16-18 mm, thereby providing a larger area for a fenestration, as described above. The distal ends 64 and 82 can each have a diameter of approximately 12 mm. However, it will be appreciated that various other diameters could be used to allow for appropriate mating between the various limb extensions and the limbs 18a and 18b.

Figure 4:
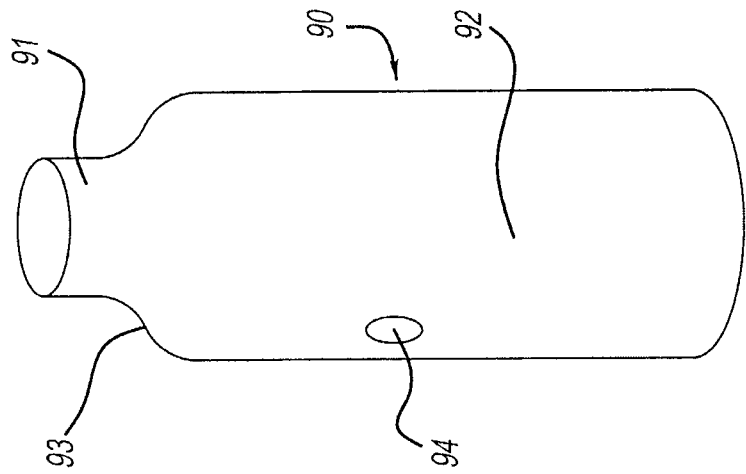
FIG. 4 is a perspective view of an alternative embodiment of a limb extension.

In another form as shown in FIG. 4, a limb extension 90 can include a proximal region 91 and a distal region 92, with a tapered portion 93 disposed therebetween. In this form, a fenestration 94 is disposed in the distal region 92, similar to the fenestration 86 disposed in the intermediate region 83 of the limb extension 80. However, unlike the limb extension 80, the limb extension 90 does not taper down distally. Thus there is a larger diameter at the distal region 92 of the limb extension 90 relative to the proximal region 91. In this form, the diameter of the proximal region 91 can be approximately 12 mm, while the diameter of the distal region 92 can be approximately 16-18 mm.

In the embodiment illustrated in FIG. 1A, the limbs 18a and 18b of the graft distal end 16 extend approximately the same distance from the bifurcation point 32. For example, in one form, the limbs 18a and 18b are approximately 2-2.5 cm long. However, other lengths could also be used for the limbs 18a and 18b while remaining approximately the same length.

Figure 5:
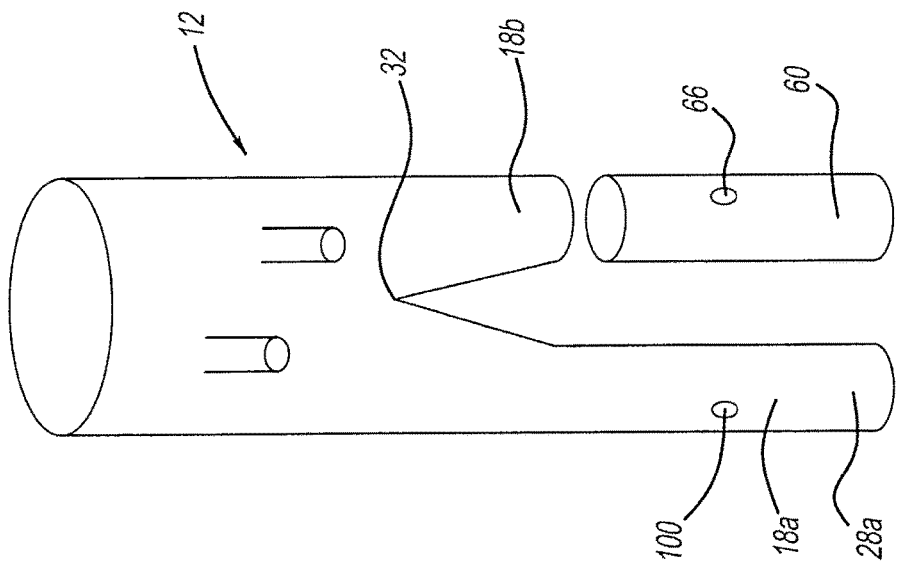
FIG. 5 is an exploded view of an another embodiment of an endoluminal prosthesis having a graft and limb extension for mating thereto.

In another form, the prosthesis 10 can include limbs 18a and 18b that have different lengths, as shown in FIG. 5. For purposes of discussion, limb 18a will be described as being longer; however, either limb 18a or 18b could be the longer limb.

In this form, limb 18a will extend further from the bifurcation point 32 than limb 18b. A fenestration 100 can be disposed between the bifurcation point 32 and the distal end 28a of the limb 18a. The style and shape of the fenestration 100 can be similar to the fenestrations previously described, such as an inner or outer pivot fenestrations or a diamond fenestration. The fenestration 100 is preferably disposed on an outboard surface of the limb 18a, radially away from the limb 18b so that the fenestration 100 can be positioned generally adjacent the aortic wall and branches extending therefrom, such as the left renal artery or right renal artery. In this form, a single limb extension 60 can be used, rather than using two as described above, due to the limb 18a extending a longer length than limb 18b and including the fenestration 100 therein. In one form, limb 18a extends approximately 5-25 cm and limb 18b extends approximately 2-2.5 cm from the bifurcation point 32.

The endoluminal prosthesis 10 may be provided as part of a preloaded system that comprises a first wire 200 having proximal and distal regions 202 and 204, which is configured to facilitate insertion of the endoluminal prosthesis 10 into the aortic artery.

Figure 6:
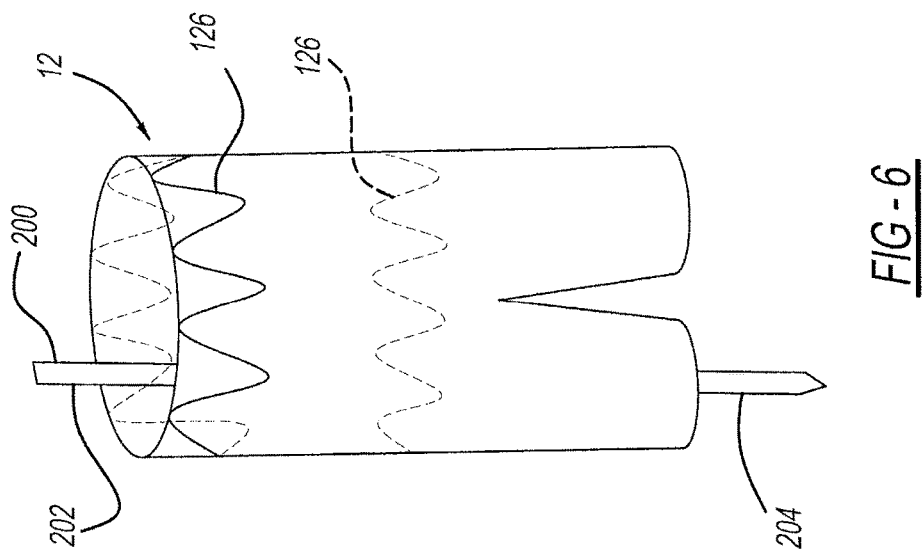
FIG. 6 is a perspective view of the graft of FIG. 1A showing a wire guide extending therethrough and stents mounted thereon.

The endoluminal prosthesis 10 further comprises at least one stent coupled to the graft 12. As illustrated in FIG. 6, a plurality of stents 126 may be coupled to an outer surface of the graft 12 along the length thereof. However, the plurality of stents 126 can alternatively be coupled to an inner surface of the graft 12, or some of the plurality of stents 126 could be coupled to the inner surface while the other stents 126 are coupled to the outer surface. It will be appreciated the number of stents 126 and the coverage of the graft by the stents 126 can vary depending on the needs of the user.

The stents 126 may be made from numerous metals and alloys. In one example, the stents 126 comprise a shape-memory material such as a nickel-titanium alloy ("nitinol"). Moreover, the structure of the stents 126 may be formed in a variety of ways to provide a suitable intraluminal support structure. For example, one or more stents may be made from a woven wire structure, a laser-cut cannula, individual interconnected rings, or another pattern or design.

In the example of FIG. 6, the stents 126 may be configured in the form of one or more "Z-stents" or Gianturco stents, each of which may comprise a series of substantially straight segments interconnected by a series of bent segments. The bent segments may comprise acute bends or apices. The Gianturco stents are arranged in a zigzag configuration in which the straight segments are set at angles relative to each other and are connected by the bent segments. However, as noted above, the stents 126 may comprise any suitable configuration and one or more stents may be provided.

Similarly, the various limb extensions 60, 80, or 90 may have a construction similar so that described above with respect to the graft 12. For example, a plurality of stents 126, having any of the compositions or shapes described above, may likewise be used, either on the inner or outer surface of the particular limb extension.

The graft 12 has a compressed, reduced diameter delivery state in which it may be advanced to a target location within a vessel, duct or other anatomical site, such as the abdominal aorta near the celiac artery CA and superior mesenteric artery SMA, as shown in FIGS. 7-15 below. The graft 12 further has an expanded state, as shown in FIG. 1A, in which it may be configured to apply a radially outward force upon the vessel, duct or other target location. In the expanded state, fluid flow is allowed through the lumen 24 of the graft 12. The previously described dimensions of the graft 12 generally refer to its expanded state. Thus, in the compressed delivery state, the diameters listed above will be smaller.

Similarly, the limb extensions 60, 80, and 90 have a compressed, reduced diameter delivery state in which they may be advanced to the target location within a vessel, duct, or other anatomical site, such as the abdominal aorta near the renal arteries and the iliac arteries. Furthermore, the limb extensions 60, 80, and 90 can be configured to apply a radially outward force upon the vessel, duct, or target location, and also upon an inner surface of the limbs 18a or 18b to which the limb extension is mated. Alternatively, the limbs 18a and 18b of the graft can be configured to apply a radially outward force on an inner surface of the limb extensions 60, 80, and 90 for mating. When both the graft 12 and limb extensions 60, 80, or 90 are in the expanded state and mated, fluid flow is allowed through the lumen 24 of the graft 12, through the limbs 18a and 18b, and through the limb extension lumens 65.

For securing the graft 12 within the patient's anatomy, the graft 12 can include a bare stent (not shown) extending from the proximal end 20 of the proximal portion 14, with the bare stent configured to expand outward to engage the body vessel wall in a manner known in the art. Alternatively, or in addition to the bare stent, the graft 12 can include one or more barbs (not shown) extending through the graft material for engaging the body vessel wall and retaining the graft 12 in place in a manner known in the art.

Similarly, the various limb extensions described herein can likewise include barbs extending outwardly therefrom to engage the body vessel wall when expanded.

Figure 7:
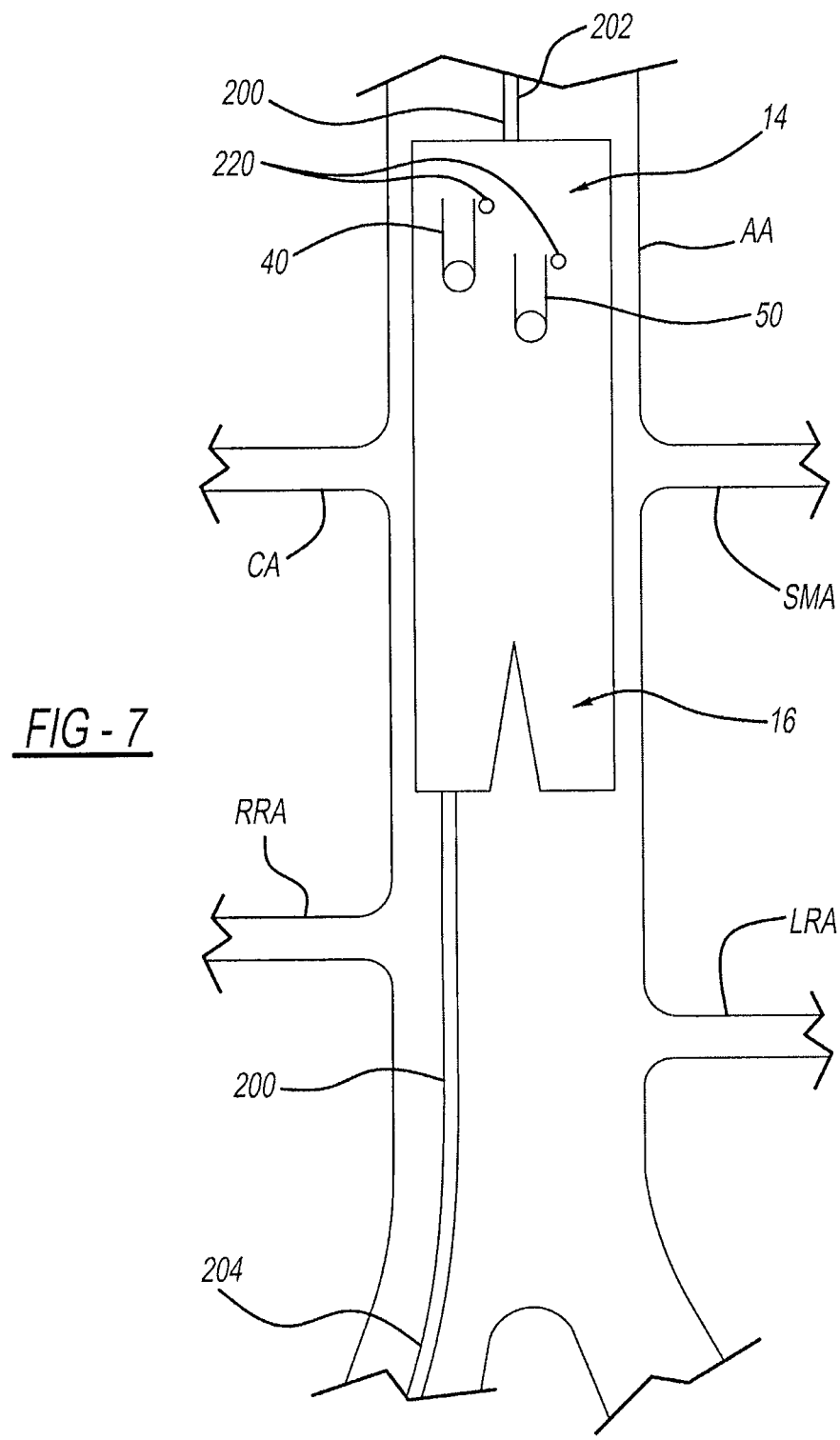
FIGS. 7-15 illustrate side views of exemplary method steps of using the endoluminal prosthesis of FIG. 1A-6, with the aorta and branch vessels shown cut-away.

One or more radiopaque markers 220, shown in FIG. 7, may be provided to provide radiographic visualization of the position of the graft 12 when placed in the vessel or duct of a patient. A plurality of radiopaque markers 220, which according to one example may be provided in the form of gold beads, are coupled to the graft 12 and/or stents 126 to facilitate imaging of various desired locations along the length of the endoluminal prosthesis 20. The radiopaque markers 220 are shown in FIG. 7 as identifying the location of the branches 40 and 50, but it will be appreciated that a plurality of radiopaque markers can be disposed at various locations on the graft 12, limb extensions 60, 80 and 90, or other complementary components to identify their respective positions within a patient's anatomy, as desired.

Similarly, a plurality of markers 222 may be provided on the limb extensions 60, 80 and 90 to provide radiographic visualization of the position and circumferential orientation of the limb extensions 60, 80, and 90 relative to the graft 12 and the anatomical site. In one form, as shown in FIG. 2, the markers 222 can be aligned longitudinally on one of the limb extensions 60, 80, and 90 at a location approximately 90 degrees from the fenestration 66, 86, or 96 therein. Thus, the fenestration 66, 86, or 96 can be oriented to the left or right by orienting the markers 222 either at either 0 degrees or 180 degrees within the vessel.

Referring now to FIGS. 7-15, exemplary method steps for using the prosthesis of FIG. 1A to treat a condition in the area of a patient's abdominal aorta AA and/or branch vessels are shown and described. In a first step, the graft 12 is provided with first wire 200 coupled to the graft 12 in the preloaded configuration shown in FIG. 1A. The graft 12 is compressed into a delivery state, and is delivered into the patient's abdominal aorta AA using a suitable deployment system or introducer. An introducer, such as that described in PCT application WO98/53761, entitled "A Prosthesis and a Method and Means of Deploying a Prosthesis," which is incorporated herein by reference in its entirety, may be used to deploy the graft 12. PCT application WO98/53761 describes a deployment system for an endoluminal prosthesis whereby the prosthesis is radially compressed onto a delivery catheter and is covered by an outer sheath. To deploy the system, the operator slides or retracts the outer sheath over the delivery catheter, thereby exposing the graft 12. The graft 12 expands outwardly upon removal of the sheath. The operator can directly manipulate the sheath and the delivery catheter, which provides the operator with a relatively high degree of control during the procedure. Further, such delivery devices may be compact and may have a relatively uniform, low-diameter radial profile, allowing for atraumatic access and delivery.

Using such a suitable delivery system, a physician may obtain access to the abdominal aorta AA via a femoral cut-down when the graft 12 is in the compressed state. The endoluminal prosthesis 20 is positioned within the abdominal aorta AA in the compressed state, for example, using the radiopaque markers 220, such that the branches 40 and 50 are generally aligned in the vicinity of the ostiums of the celiac artery CA and superior mesenteric artery SMA, respectively, as depicted in FIG. 7. In one form, the graft 12 is positioned so that the branches 40 and 50 are approximately 2 cm proximally from the arteries CA and SMA. At this time, a sheath of the delivery system that constrains the endoluminal prosthesis 20 may be retracted distally to allow the stents 126, and the graft 12 coupled thereto, to attain the expanded deployed configuration shown in FIG. 7.

It should be noted that, in FIGS. 7-15, outer surfaces of the graft 12 are not shown as being in contact with inner surfaces of the abdominal aorta AA solely for illustrative purposes. In use, the graft 12 is sized and configured so that at least an outer surface of the proximal region 14 securely engages an inner surface of the abdominal aorta AA to hold the graft 12 in place relative to the vasculature. Additional outer regions of the graft 12 may securely engage the inner surface of the abdominal aorta AA. As described above, the graft 12 can securely engage the abdominal aorta AA using a bare stent, barbs, or a combination of both.

After the graft is securely deployed within the patient's abdominal aorta AA, a user may then snare the proximal region 202 of the first wire 200, via arm access using the brachial artery, to pull the proximal region 202 of the first wire 200 through the brachial artery and out of the patient's arm. This achieves "through and through" access where the proximal region 202 of the first wire 200 is accessible outside of the brachial arteries, while the distal region 204 of the first wire 200 is accessible outside of the femoral arteries.

Figure 8:
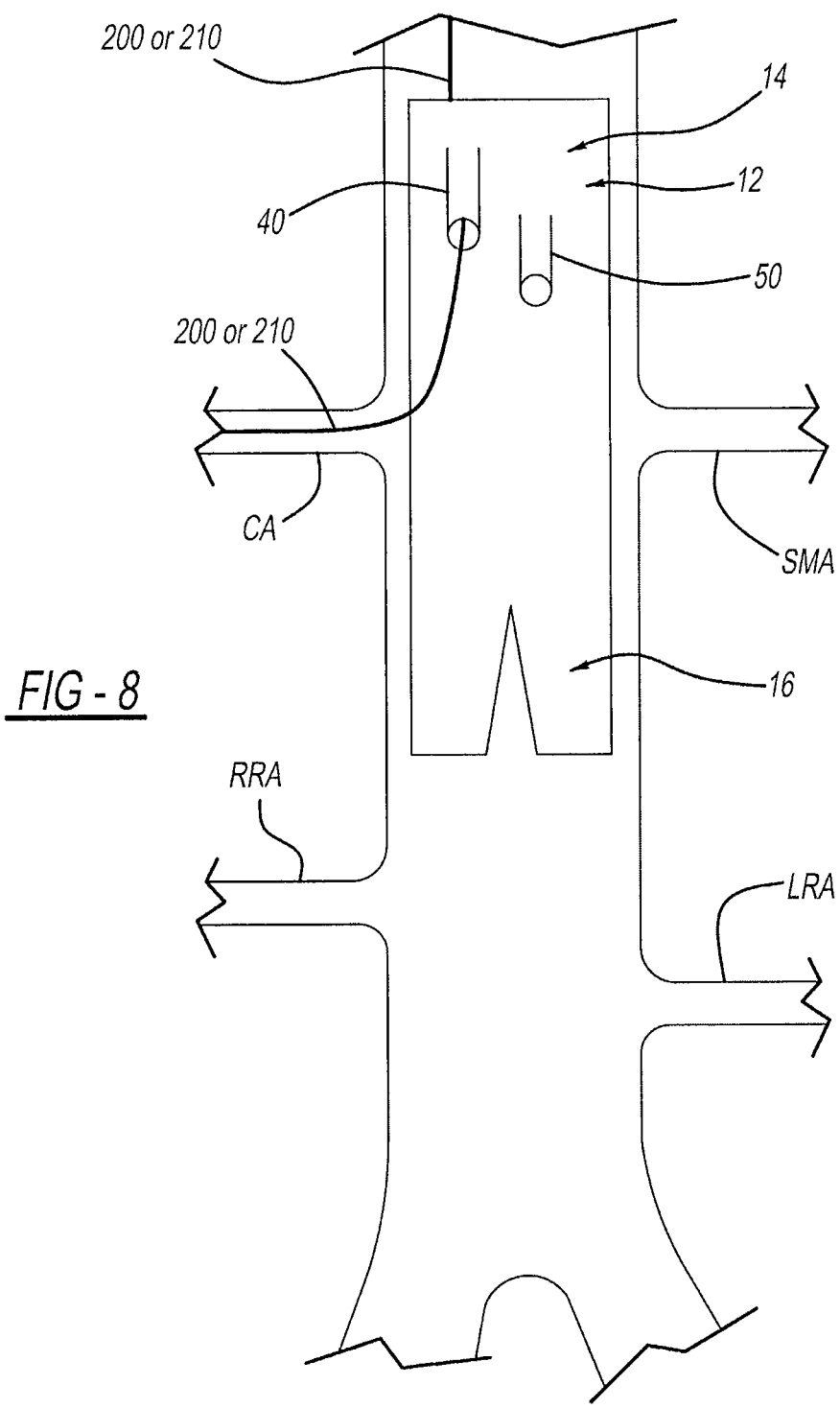

Referring now to FIG. 8, at this stage, another wire guide 210 may be introduced and manipulated so that it enters the celiac artery CA, as shown in FIG. 8. Alternatively, the first wire 200 could remain within the vasculature and the graft 12 and subsequently repositioned to that it enters the celiac artery CA similar to the positioning shown in FIG. 8.

Figure 9:
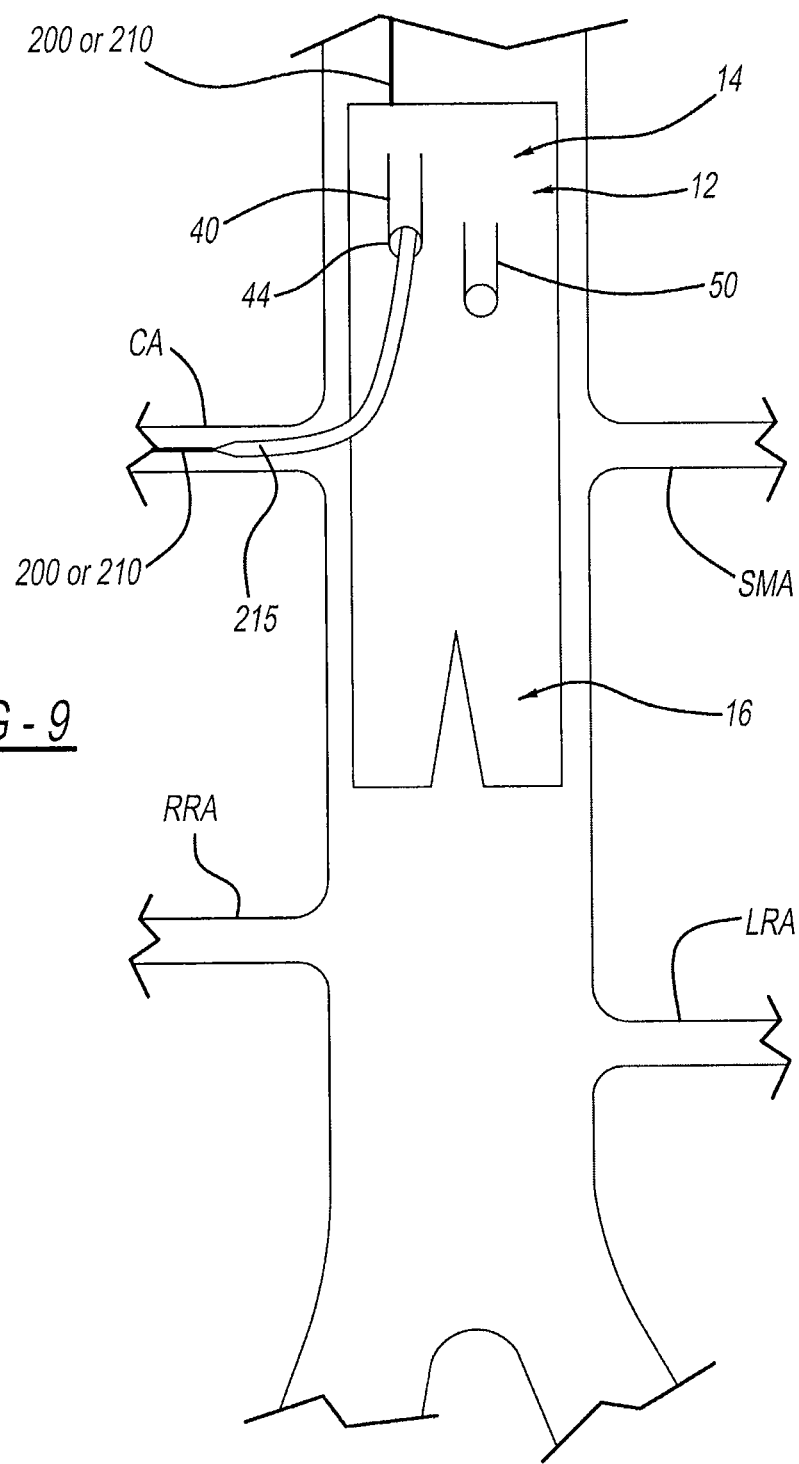

Referring to FIG. 9, a further deployment device 215 can then be introduced via the wire guide 210, such that the deployment device 215 is advanced in a distal direction from the brachial artery and ultimately into the celiac artery CA. The deployment device 215 extends out of the distal end 44 of the first branch 40 of the graft 12 so that a branch extension prosthesis 240 of FIG. 10 can be deployed to extend from the first branch 40 of the graft 12 into the celiac artery CA.

Figure 10:
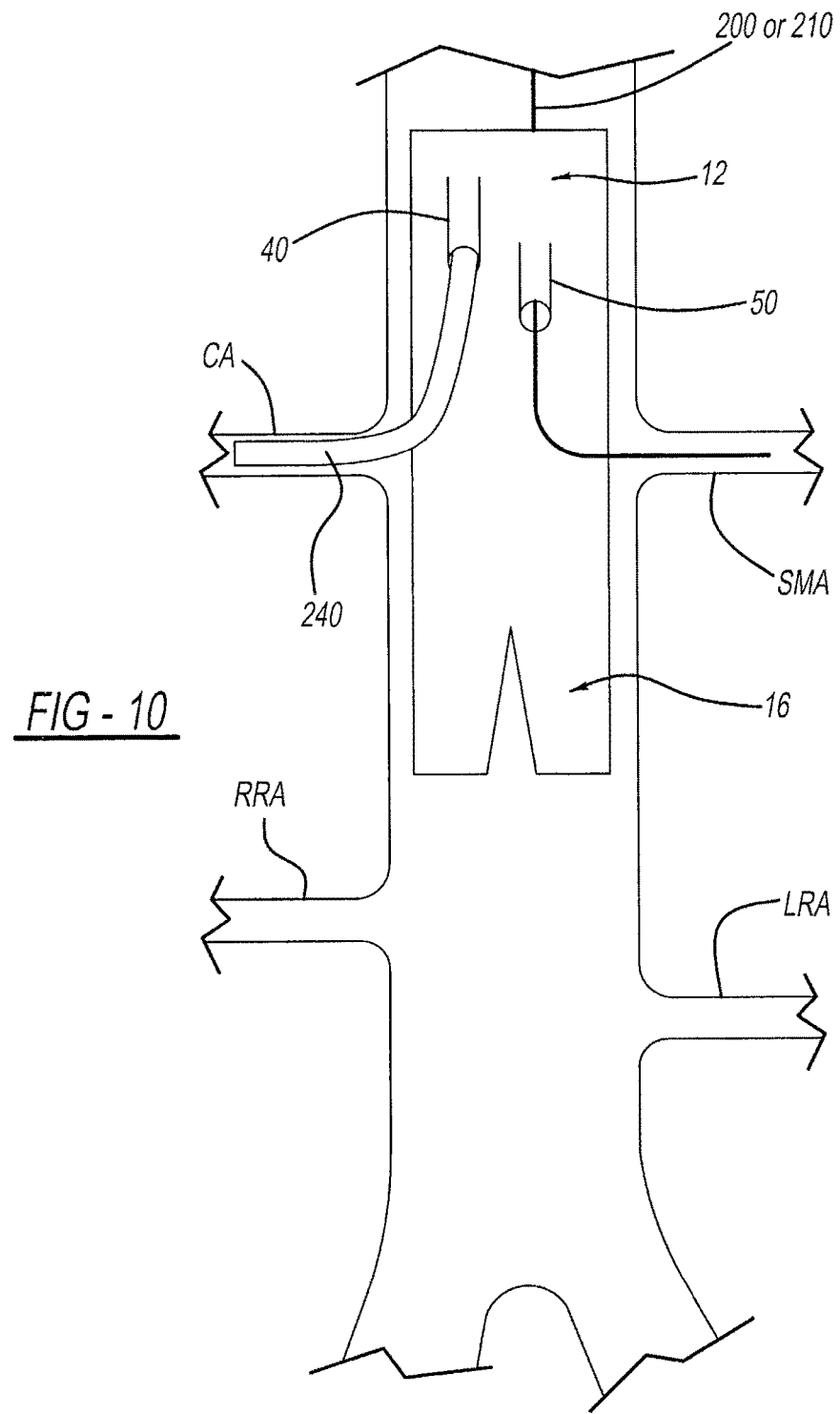

Referring to FIG. 10, upon deployment from the deployment device 215, the branch extension prosthesis 240 and the first branch 40 of the graft 12 are mated such that there is a suitable tromboning connection, preferably with a 1.5 to 2 cm overlap and a 1 mm or less difference in diameter at the interconnection. Optionally, the devices may be expanded for about 30 seconds using a suitably sized balloon dilation catheter. At this time, the branch extension prosthesis 240 provides patent fluid flow through the graft 12 into the celiac artery CA.

The branch extension prosthesis 240, along with the branch extension prostheses 250, described below, may comprise a suitable graft or stent-graft to direct flow from the graft 12 into the arteries CA and SMA. By way of example and without limitation, the branch extension prostheses 240 and 250 may include the Fluency® Plus Vascular Stent Graft from Bard Peripheral Vascular, Helsingborg, Sweden, or the Jostent® Peripheral Stent Graft from Abbott Vascular of Abbott Park, Ill.

In a next step, the wire guide 210 is proximally retracted away from the celiac artery CA and the distal end of wire guide 212 is positioned just proximal to the second branch 50 at a location adjacent to the SMA. The wire guide 110 is then advanced in a distal direction into the superior mesenteric artery SMA, as shown in FIG. 10. Alternatively, if the first wire 200 has been retained, the first wire 200 can be positioned and advanced into the superior mesenteric artery in a similar fashion.

Figure 11:
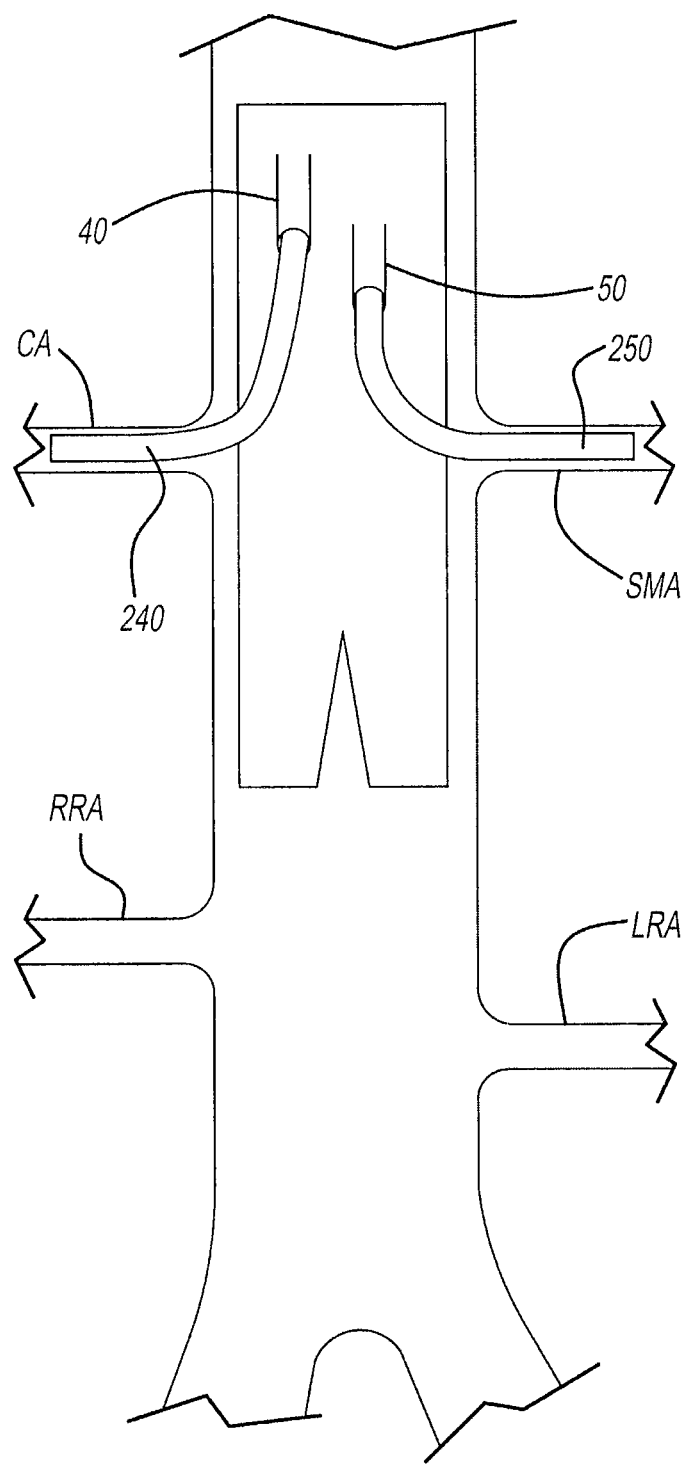

Referring now to FIG. 11, in a next step, the sequence shown in FIGS. 9-10 may be repeated whereby the deployment device 215 of FIG. 9 is introduced via the wire guide 210 or 200 in a distal direction from the brachial artery and ultimately into the superior mesenteric artery SMA. The deployment device 215 extends out of the distal end 54 of the second branch 50 of the graft 12 so that a branch extension prosthesis 250 can be deployed to extend from the second branch 50 of the graft 12 into the superior mesenteric artery SMA. Upon deployment from the deployment device 215, the branch extension prosthesis 250 and the second branch 50 of the graft 12 are mated such that there is a suitable tromboning connection in the manner described above. At this time, the branch extension prosthesis 250 provides patent fluid flow through the graft 12 into the superior mesenteric artery SMA, and the wire guide 210 may be removed, as shown in FIG. 11.

At this time, the graft 12 is positioned, along with the branch extensions 240 and 250, to provide fluid flow to the arteries CA and SMA. The limbs 18a and 18b are positioned proximally from the ostiums of the renal arteries LRA and RRA so that the limb extensions 60 may be introduced and mated with the limbs 18a and 18b, with the fenestrations 66 aligned with the corresponding renal artery LRA or RRA.

Figure 12:
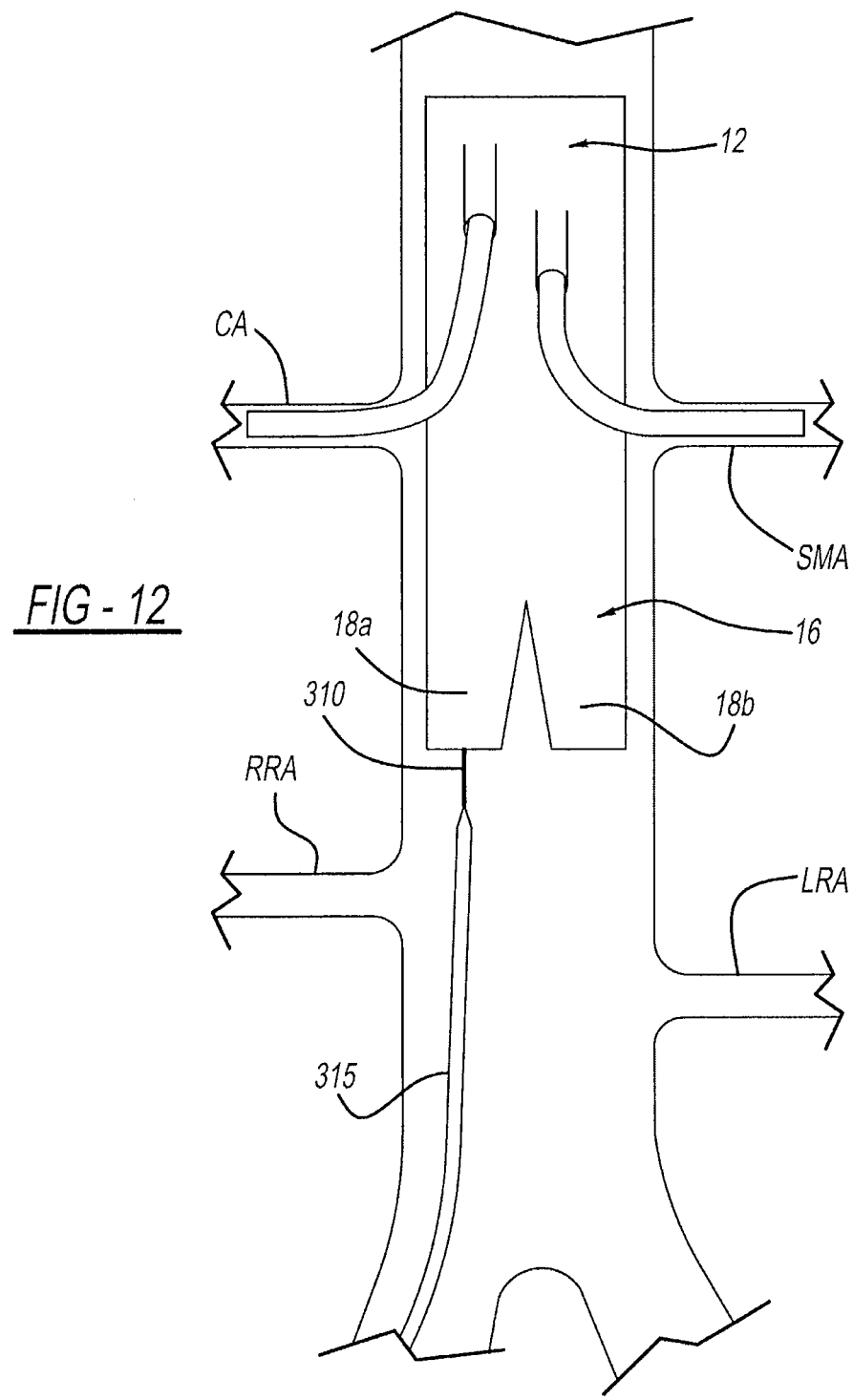

Referring now to FIG. 12, in a next step, a wire guide 310 is introduced through the femoral artery and through the lumen 30a of the limb 18a. A deployment device 315 is introduced via the wire guide 310 in a proximal direction from the femoral artery and ultimately into the limb 18a. The deployment device 315 carries the limb extension 60 in a compressed configuration. Upon deployment from the deployment device 315, the limb extension prosthesis 60 and the limb 18a are mated such that there is a suitable tromboning connection, preferably with a 1.5 to 2 cm overlap and a 1 mm or less difference in diameter at the interconnection. Optionally, the devices may be expanded for about 30 seconds using a suitably sized balloon dilation catheter. At this time, the limb extension 60 can provide patent fluid flow through the limb 18a and into the limb extension 60.

Figure 13:
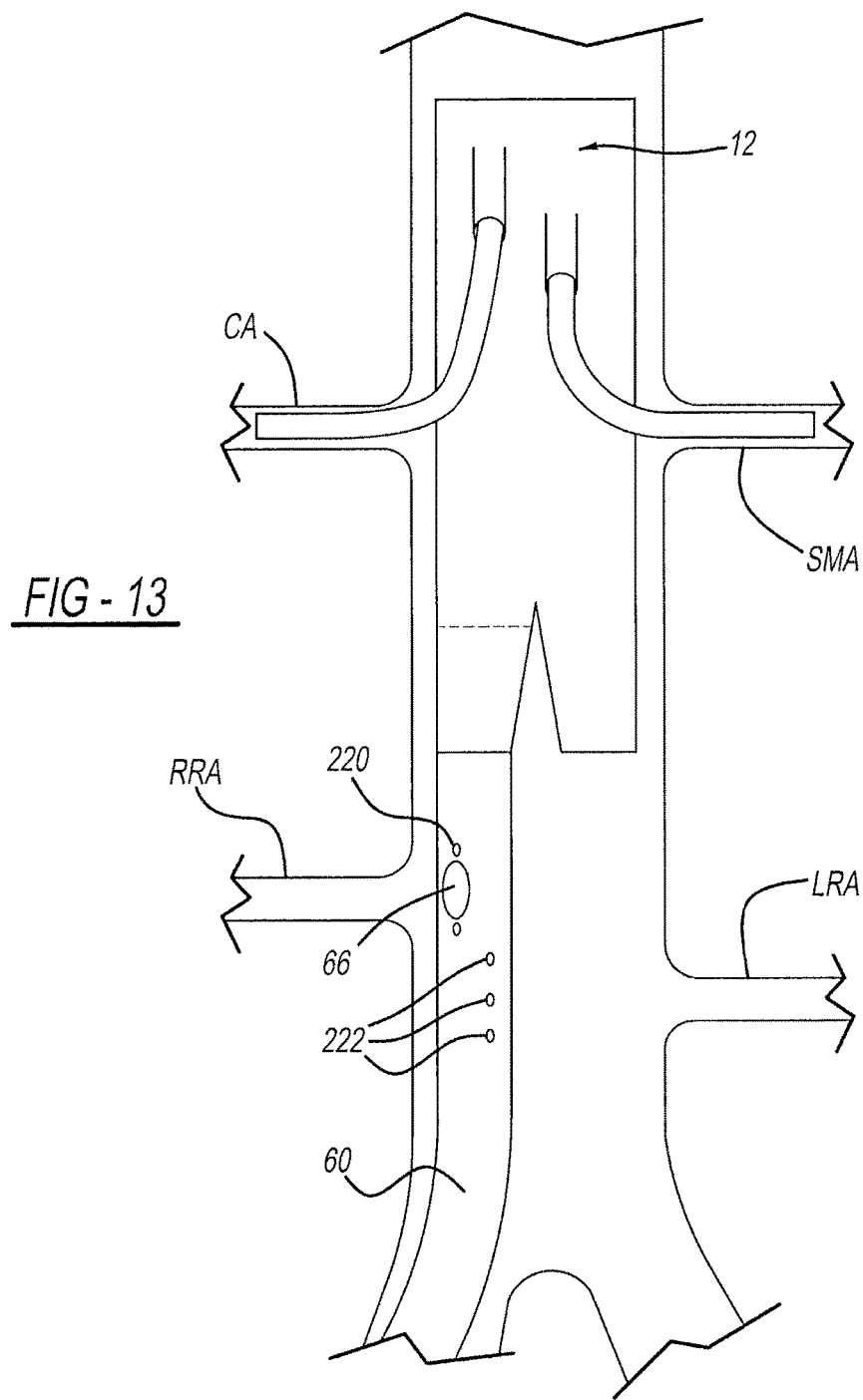

With reference to FIG. 13, during deployment, a user can monitor the position and orientation of the limb extension 60, including the fenestration 66 therein, via the radioactive markers 222. Based on the position, the user can adjust the longitudinal and circumferential orientation of the limb extension 60 prior to mating to align the fenestration 66 with the ostium of the right renal artery RRA. For example, in a complex anatomy, it may be necessary to adjust the limb extension 60 proximally if the fenestration 66 is distally below the right renal artery RRA during deployment. Moreover, the ostium of the right renal artery RRA may be positioned at a different circumferential orientation than the circumferential orientation of the fenestration 66. By monitoring the markers 222, the user can rotate the limb extension 60 to align the fenestration 66 with the ostium of the right renal artery RRA.

Another limb extension 60 can deployed and adjusted in the same fashion as described above, except that the this limb extension 60 is adjusted to align with the left renal artery LRA and is mated with the limb 18b. Prior to delivery of this limb extension 60, the wire guide 310 can be retracted distally and subsequently advanced into limb 18b, or the wire guide 310 could be fully retracted from the patient's body and a new wire guide could be delivered. Of course, it will be appreciated that the order of delivering the limb extensions 60 could be altered such that the first of the two limb extensions 60 is delivered to the limb 18b. In the same fashion, it will be appreciated that alternative limb extensions 80 and 90 could be used in place of either or both limb extensions 60 if desired.

Figure 14:
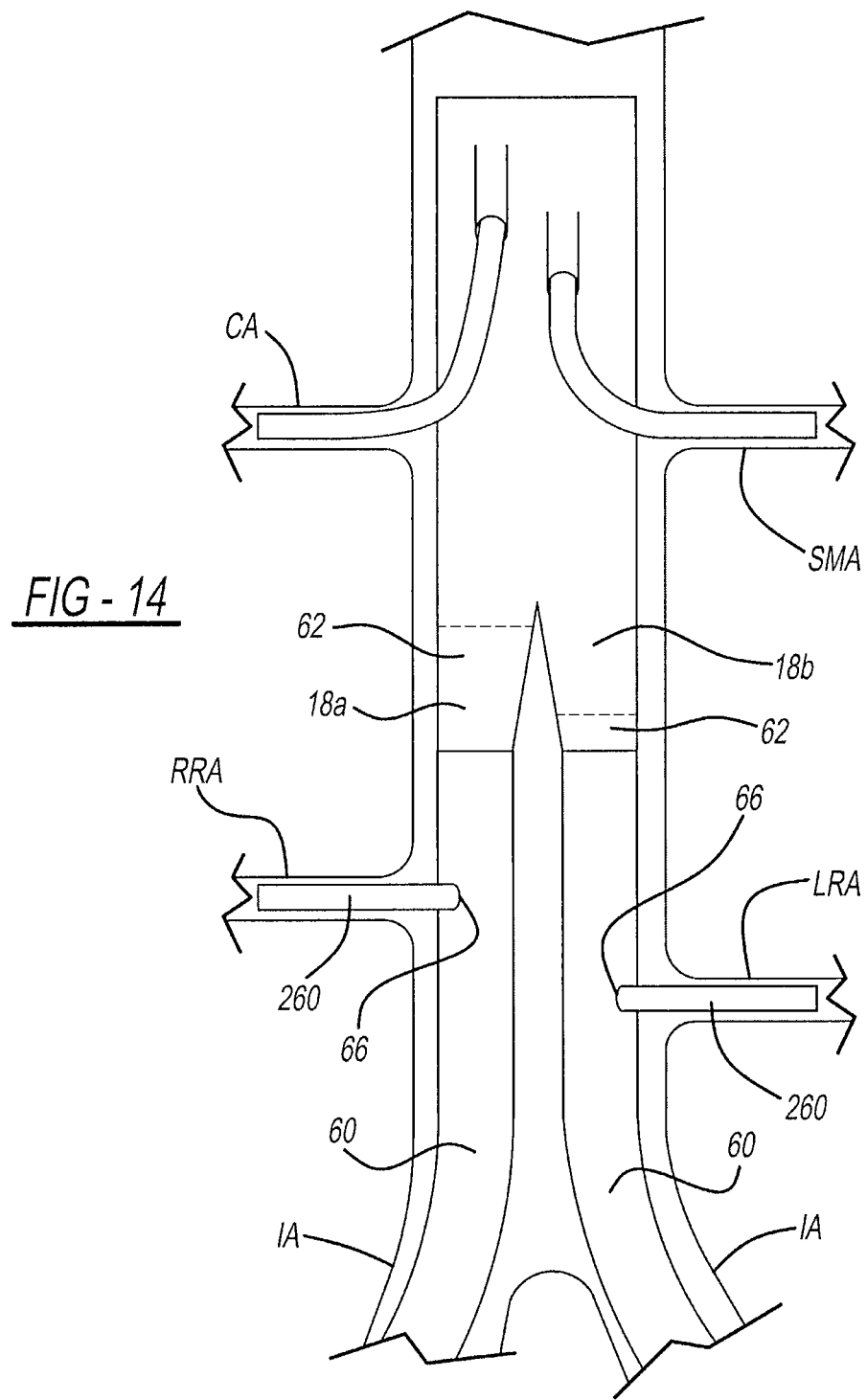

Referring now to FIG. 14, when deployed, the limb extensions 60 will exert a radial force on the limbs 18a and 18b. Additionally, the limb extensions 60 will exert a radially outward force on the iliac arteries IA located distally below the limbs 18a and 18b of the deployed graft 12. Once both limb extensions 60 have been deployed and mounted, patent fluid flow is provided through the limbs 18a and 18b and through the limb extensions 60. In some instances, the limb extension 60 may not be long enough to extend sufficiently into the iliac arteries. In this case, additional limb extensions (not shown) having a tubular form, and without fenestrations therein, can be delivered to extend between the distal end 64 of the limb extension 60 and the corresponding iliac artery IA. When these additional extensions have been deployed, patent fluid flow can thereby be provided to the iliac arteries.

At this point, the graft 12 and limb extensions 60 are expanded and positioned in place. The fenestrations 66 are oriented with the corresponding renal arteries LRA and RRA. As shown in FIG. 14, renal branch extensions 260 may be delivered to the renal arteries in the manner described in U.S. patent application Ser. No. 13/213,349, filed Aug. 19, 2011, which is hereby incorporated by reference in its entirety. The various pivot fenestrations described therein provide for the renal branch extensions 260 to reliably mount to the fenestrations 66 in the event that the fenestrations 66 are slightly misaligned with the renal arteries LRA or RRA.

Once the renal branch extensions 260 have been deployed, the endoluminal prosthesis 10, with its components in their deployed and radially expanded state, will provide patent fluid flow from the abdominal aorta AA to the various branches, such as the celiac artery CA, the superior mesenteric artery SMA, the left renal artery LRA, the right renal artery RRA, and the iliac arteries. The modular nature of the endoluminal prosthesis 10 allows a user to efficiently deploy the prosthesis to myriad types of complex anatomy without the need to manufacture unique prosthesis prior to deployment. This configuration allows for an "off-the-shelf" solution to repairing previously installed endografts that have failed or to repair aneurysms.

The above description of the delivery of the endoluminal prosthesis 10 has related to a prosthesis having a graft 12 with two relatively short limbs 18a and 18b. However, as described previously, other forms of grafts 12 can also be used.

Figure 15:
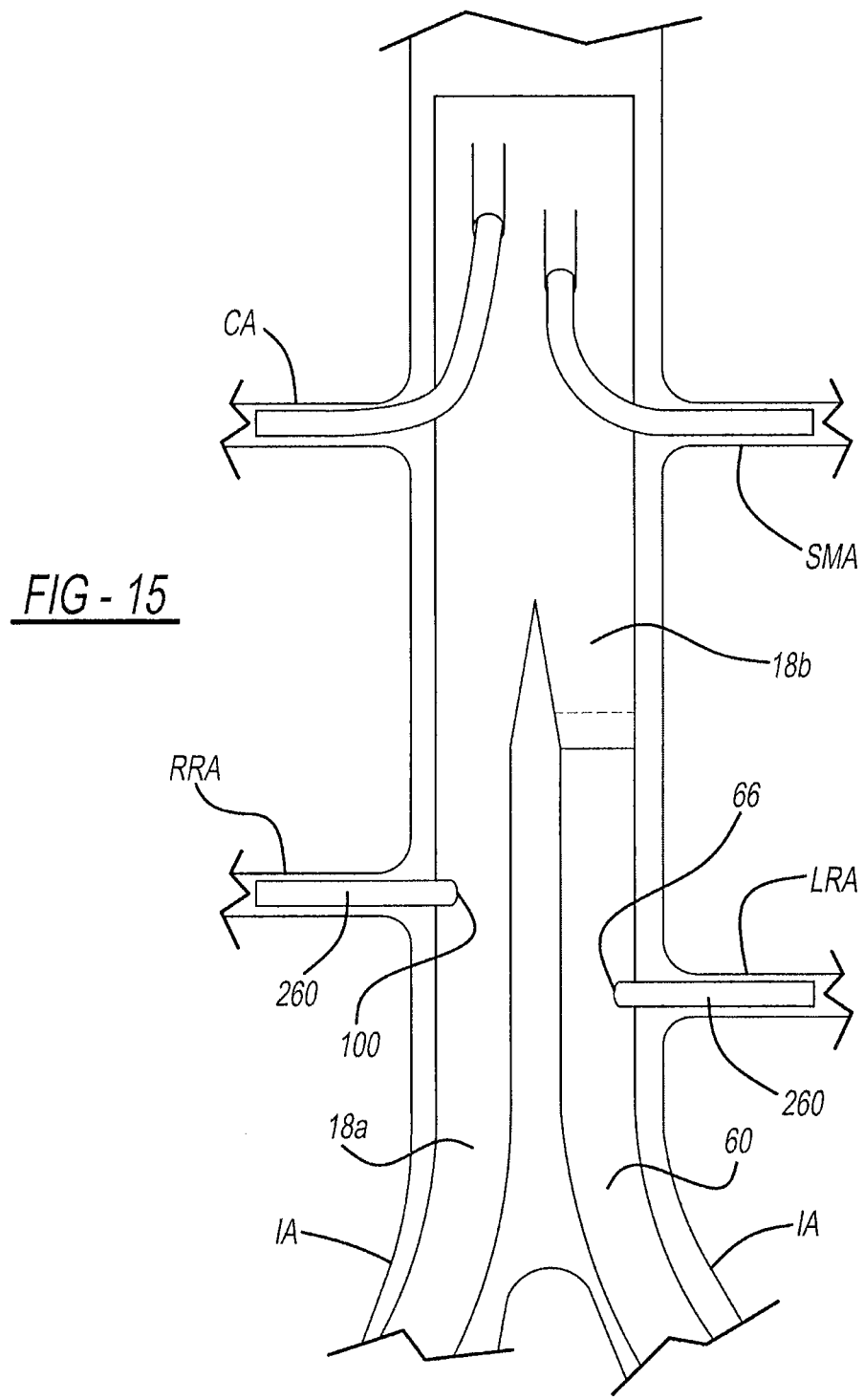
Figure 16:
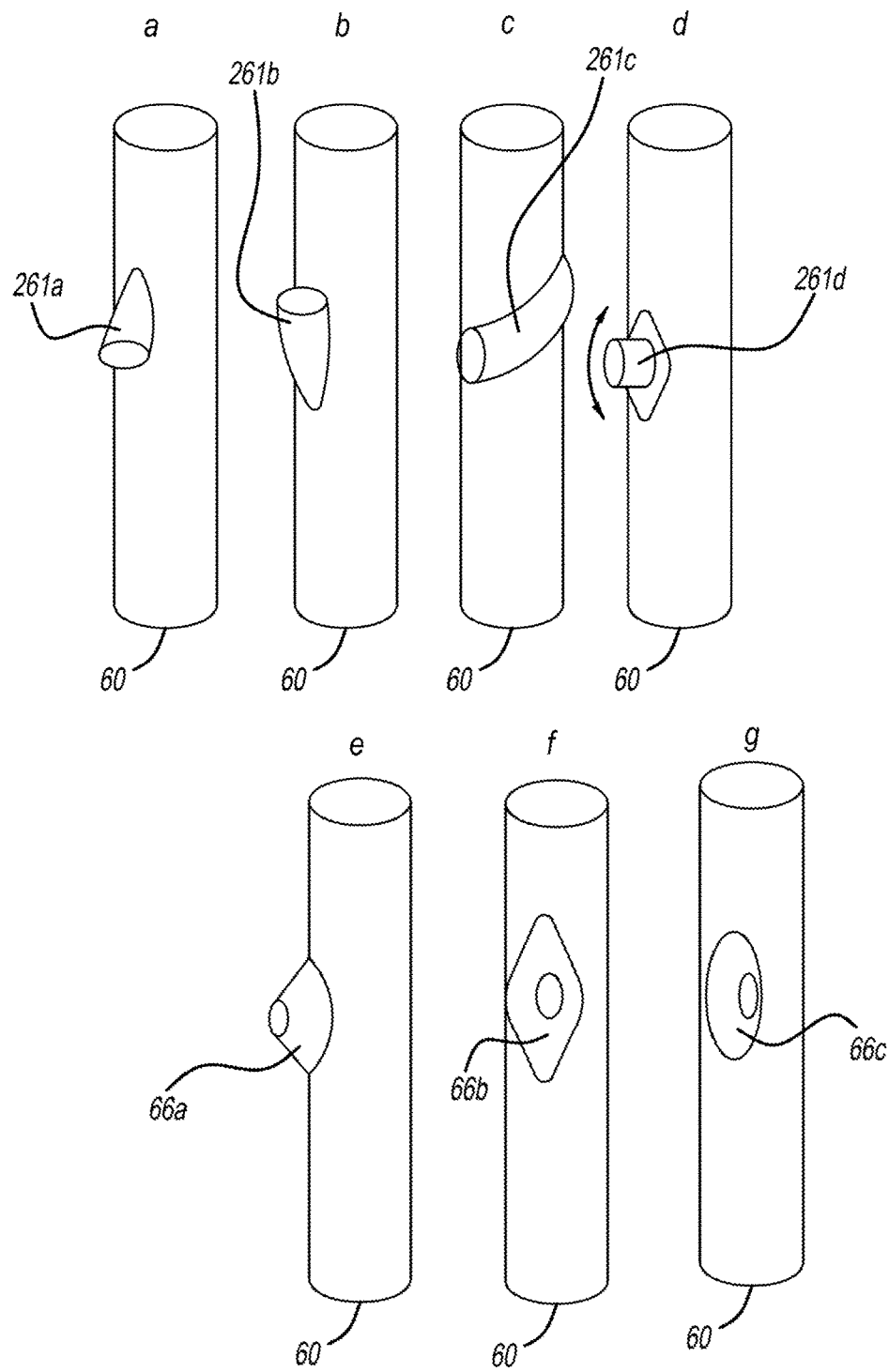

For example, with reference to the graft 12 illustrated in FIG. 15, the limb 18a extends further in the distal direction from the bifurcation point 32 than the limb 18b. In this form, the graft 12 is compressed into its delivery state and delivered to the anatomical site as previously described. However, rather than align the graft 12 such that the branches 40 and 50 are adjacent the celiac artery CA and the superior mesenteric artery SMA, the graft 12 is aligned such that the fenestration 100 in the limb 18a is aligned with the corresponding renal artery. For example, as shown in FIG. 15, the fenestration 100 is aligned with the ostium of the right renal artery RRA. The limb extension 60 is subsequently delivered aligned with the other renal artery (the left renal artery LRA in the example shown in FIG. 15) and mated with the limb 18b in the manner described above. This configuration and method of delivery may be suitable for some patients where the location of one renal artery requires the adjustable positioning of the limb extension 60, but the location of the fenestration 100 in the longer limb 18a is sufficient to align it with the ostium of the other renal artery while still maintaining adequate positioning of the branches 40 and 50 relative to the arteries CA and SMA. It will be appreciated that the steps described above regarding renal branch extensions 260 as shown in FIG. 14 could be similarly performed for this embodiment.

Similarly, in patients having only one kidney, it may be unnecessary to position a fenestration in a limb extension with the corresponding renal artery. In such patients, a graft 12 having a longer limb 18a can be delivered in the manner described above. In this case, the limb 18a may not include a fenestration therein. Thus, the subsequent delivery and positioning of the single limb extension 60 is sufficient to align the fenestration 66 therein with the renal artery corresponding to the patient's kidney. The longer limb 18a having no fenestration may facilitate a faster delivery and deployment of the graft 12 because it does not require precise positioning of a fenestration with the inactive renal artery.

With reference to FIGS. 16a-g, various types and shapes of the fenestrations 66 are illustrated: an everted pivot fenestration 66a; a diamond pivot fenestration 66b; and a standard pivot fenestration 66c. Alternatively, or in combination with the various types of fenestrations 66, the limb extension 60 can include at least one of the various types of the illustrated intermediate branch extensions including: a downward branch 261a; an upward branch 261b; a helical/angled branch 261c; and a steerable branch 261d. The intermediate branch extensions types could also be used for the first and second branches 40 and 50 that are generally aligned with the CA and SMA arteries, previously described above. It will also be appreciated that these fenestration types and intermediate branch extension types could be used with the longer limb 18a that is shown in FIG. 15. These various fenestrations and intermediate branch extensions could also be used with the embodiments illustrated in FIGS. 3 and 4 and for performing the method steps of FIGS. 7 through 14. The various fenestrations and intermediate branch extensions described herein can be referred to generically as passageways.

Of course, it will be appreciated that other configurations of the graft 12 and limbs 18a and 18b may be employed depending on the particular patient's anatomy. The modular nature of the limb extensions 60 and the graft 12 allows for a user to select in an "off-the-shelf" manner the components necessary to fit the particular patient's anatomy.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:
1. A modular stent-graft apparatus, the apparatus comprising:
   a graft comprising biocompatible material, the graft having a proximal and distal end;
   a generally tubular proximal portion of the graft with a lumen extending therethrough;
   a first branch extending distally from the graft proximal portion;
   a second branch extending distally from the graft proximal portion;
   first and second limb portions of the graft extending distally from a bifurcation point of the proximal portion and having distal ends, the first and second limb portions each having lumens extending therethrough, the lumens of the limb portions being in fluid communication with the proximal portion lumen;
   at least one limb extension comprising biocompatible material, the at least one limb extension having a proximal end and a distal end and a lumen extending therebetween, the at least one limb extension dimensioned to engage one of the first and second limb portions; and
   at least one passageway though a sidewall of the at least one limb extension disposed between the proximal and distal ends of the at least one limb extension;
   wherein the first and second branches each have proximal and distal ends and a lumen extending therebetween that is in fluid communication with the graft proximal portion lumen; and
   wherein the first and second branches are disposed proximally from the bifurcation point and distally from the proximal end of the graft;
   wherein the first and second branches extend distally from the graft proximal portion outside of the graft proximal portion lumen;
   wherein the graft proximal portion and the first and second limb portions are one piece and part of a one piece single graft structure and define a bifurcated graft body such that the graft proximal portion and the first and second limb portions are deliverable as a single one piece unit;
   wherein at least a portion of the biocompatible material of the graft extends continuously from a proximal end of the proximal portion to a distal end of the first and second limb portions;
   wherein the graft has a delivery state and a deployed state, and the graft proximal portion and the first and second limb portions are part of the one piece single graft structure and compressed in the delivery state and deliverable as the one piece single graft structure while compressed, and the graft is expanded relative to the delivery state in the deployed state;
   wherein the one piece single graft structure is deliverable within a delivery sheath while compressed in the delivery state.

2. The apparatus of claim 1, wherein distal ends of the first and second limbs extend approximately the same longitudinal length from the bifurcation point.

3. The apparatus of claim 1 wherein the at least one limb extension comprises a first and second limb extension each having a passageway therein, and the first and second limb extensions are mated to the first and second limb portions.

4. The apparatus of claim 3, wherein the passageways in the first and second limb extensions are each located at approximately the same longitudinal distance from the proximal ends thereof, and the passageways are located at different longitudinal distances from the bifurcation point when the first and second limb extensions are mated to the limb portions.

5. The apparatus of claim 1, wherein the distal end of the first limb extends longitudinally farther from the bifurcation point than the distal end of the second limb, and the proximal end of the at least one limb extension is mated to the distal end of the second limb.

6. The apparatus of claim 5 further comprising a limb passageway through a sidewall in the first limb disposed between the proximal and distal ends thereof.

7. The apparatus of claim 1, wherein the passageway comprises a fenestration in the at least one limb extension.

8. The apparatus of claim 1, wherein the passageway comprises a branch extending from the at least one limb extension.

9. An endoluminal prosthesis, comprising:
   a graft having a bifurcated body comprising a biocompatible material, the graft having proximal and distal ends and a lumen extending therebetween, the bifurcated body having first and second limb portions extending distally from a generally tubular proximal portion;
   first and second distally extending branches extending from the proximal portion of the graft and outside of the lumen of the graft and providing fluid communication from the lumen of the graft; and
   a first limb extension attached to and extending distally from the first limb portion, the first limb extension having a passageway through a sidewall thereof;
   wherein the proximal portion of the graft and the first and second limb portions are one piece and part of a one piece single graft structure and the one piece single graft structure is compressed and in a delivery state and deliverable within a delivery sheath as the one piece single graft structure while compressed, and is expanded relative to the delivery state in a deployed state;
   wherein at least a portion of the biocompatible material of the graft extends continuously from a proximal end of the proximal portion to a distal end of the first and second limb portions while compressed in the delivery state.

10. The prosthesis of claim 9 wherein the first limb extension includes a proximal portion and a distal portion, the proximal portion having a smaller diameter than the distal portion when the first limb extension is in a radially expanded condition.

11. The prosthesis of claim 9 wherein the first limb extension includes a proximal portion, a distal portion, and an intermediate portion therebetween, the proximal and distal portions having diameters that are smaller than the intermediate portion when the first limb extension is in a radially expanded condition.

12. The prosthesis of claim 11 wherein the intermediate portion of the first limb extension is greater than the diameter of the first limb portion.

13. The prosthesis of claim 9, wherein the second limb portion includes a second passageway through a sidewall thereof.

14. A method of delivering an endoluminal prosthesis to a patient's body, the method comprising the steps of:
delivering a bifurcated body having a proximal portion and a distal portion to a vessel of a patient's body, wherein the bifurcated body defines a lumen therethrough and a bifurcation point and the distal portion includes first and second limb portions extending distally from the bifurcation point, and wherein the proximal portion includes a first branch extending distally from the proximal portion and a second branch extending distally from the proximal portion, the first and second branches providing fluid communication from the lumen and being disposed proximally from the bifurcation point, wherein the first and second branches are disposed outside of the lumen;
delivering, to a distal end of the first limb portion, a first limb extension having a first passageway through a sidewall thereof;
adjusting the longitudinal and circumferential location of the first passageway to correspond to a location of a first artery ostium; and
in response to adjusting the location of the first passageway, mating a proximal end of the first limb extension with a distal end of the first limb portion;
wherein the bifurcation point from which the first and second limb portions extend is disposed between a patient's renal arteries and heart.

15. The method of claim 14 further comprising:
delivering a second limb extension having a second passageway through a sidewall thereof to the second limb portion;
adjusting the longitudinal and circumferential location of the second passageway to correspond to the location of a second artery ostium; and
in response to adjusting the location of the second passageway, mating a proximal end of the second limb extension with the distal end of the limb portion.

16. The method of claim 15 further comprising:
delivering a first branch extension to the first passageway;
mating a proximal end of the first branch extension to the first passageway;
delivering a second branch extension to the second passageway; and
mating the second branch extension to the second passageway.

17. The method of claim 15, wherein the passageways in the first and second limb extensions are each located at approximately the same longitudinal distance from the proximal ends thereof, and the passageways are located at different longitudinal distances from the bifurcation point when the first and second limb extensions are mated to the limb portions.

18. The method of claim 14 further comprising:
delivering a first branch extension to the first passageway; and
mating a proximal end of the first branch extension to the first passageway.

19. The method of claim 14 further comprising:
delivering and mating a first branch extension to the first branch; and
delivering and mating a second branch extension to the second branch.

20. The method of claim 14, wherein the first and second branches are disposed above a patient's celiac and superior mesenteric arteries.

21. The method of claim 14, wherein the distal ends of the first and second limb portions extend approximately the same longitudinal length from the bifurcation point.

22. The method of claim 14, wherein the distal end of the second limb portion extends longitudinally farther from the bifurcation point than the distal end of the first limb portion.

23. The method of claim 22, wherein the second limb portion includes a limb passageway through a sidewall in the second limb portion disposed between the proximal and distal ends thereof.

24. The method of claim 23, wherein the limb passageway of the second limb portion is located a longitudinal distance from the bifurcation point that is different than a longitudinal distance of the first passageway of the first limb extension after mating the first limb extension to the first limb portion.

* * * * *